United States Patent [19]

Clements

[11] Patent Number: 5,659,247

[45] Date of Patent: Aug. 19, 1997

[54] DEVICE FOR DETECTING METAL OBJECTS PASSING THROUGH AN OPENING

[75] Inventor: Philip E. Clements, Littleton, Colo.

[73] Assignee: Denver Dynamics, Inc., Englewood, Colo.

[21] Appl. No.: 570,348

[22] Filed: Dec. 11, 1995

Related U.S. Application Data

[63] Continuation-in-part of Ser. No. 209,394, Mar. 10, 1994, Pat. No. 5,576,621.

[51] Int. Cl.$^6$ .......................... G01R 33/12; G01R 35/00; G08B 21/00; G01B 11/00
[52] U.S. Cl. ..................... 324/239; 209/549; 250/215; 324/202; 324/226; 324/262
[58] Field of Search .................... 324/202, 207.17, 324/207.26, 226, 227, 233–243, 262, 329; 235/449; 209/549, 562, 567, 570, 576–579, 926; 340/551, 568, 572, 941–943; 250/215, 561; 356/373, 375

[56] References Cited

U.S. PATENT DOCUMENTS

| 4,593,184 | 6/1986 | Bryce et al. | 235/449 |
| 4,949,037 | 8/1990 | Abe | 324/233 |
| 5,001,425 | 3/1991 | Beling et al. | 324/239 |
| 5,406,259 | 4/1995 | Manneschi | 324/239 X |

*Primary Examiner*—Gerard R. Strecker
*Attorney, Agent, or Firm*—John L. Isaac

[57] ABSTRACT

A metal detection device is disclosed and includes a housing defining a central aperture. An induction member is mounted to the housing and surrounds the aperture for generating an output voltage in response to the presence of a metal object near the induction member. A mechanism is provided for calibrating the induction member by comparing the output voltage to a reference voltage to establish a threshold voltage which is unaffected by transient fluctuations in the output voltage. A mechanism is also provided in the housing and spaced about the aperture for selectively sensing an object passing through the aperture. The sensing mechanism generates a detection signal in response to passage of an object through the aperture only upon activation of the sensing mechanism. A mechanism activates the sensing mechanism upon generation of an inductive member output voltage above the threshold voltage. Finally, a device is provided for triggering an alarm in response to the generation of the detection signal.

25 Claims, 8 Drawing Sheets

5,659,247

DEVICE FOR DETECTING METAL OBJECTS PASSING THROUGH AN OPENING

RELATED APPLICATION

This is a continuation-in-part of U.S. patent application Ser. No. 08/209,394, filed Mar. 10, 1994, now U.S. Pat. No. 5,576,621, the contents of which are specifically incorporated herein by reference.

BACKGROUND OF THE INVENTION

1. Field of the Invention

This invention relates generally to metal detection devices and, more particularly, to devices designed to detect the inadvertent disposal of metal articles into waste receptacles. Specifically, the present invention relates to a metal detector designed to detect the inadvertent disposal of metal objects such as surgical instruments into disposal receptacles particularly useful in medical facilities and the like.

2. Description of the Prior Art

One of the major problems in the health care industry today is the high cost of patient care. While many factors contribute to this cost, one of these factors is the difficulty in controlling waste in a hospital environment. In the operating room, surgical instruments are inadvertently but routinely discarded along with the disposable drapes and gowns after an operation. These expensive instruments are intended for reuse, and their disposal represents a substantial waste. In addition, theft of such instruments and small metallic objects also occurs through such disposal mechanisms. A recent survey of randomly selected hospitals revealed that such wasteful disposal and theft of surgical instruments mounted to losses between $30,000–$50,000 per year per operating room. In a typical hospital having six to ten operating rooms, such loss is substantial.

Moreover, used disposable surgical drapes and gowns, by law, are required to be deposited in a so called "red bag" designated for infectious waste. Such red bags are approximately the size of a lawn and garden trash and leaf bag. The red bags are held for use in an open position in each operating room by a bag holder, typically in the form of a wheeled cart. Hospital personnel merely wad up used drapes and gowns and stuff them into the red bag for disposal. As can be readily appreciated, valuable surgical instruments, typically fashioned from an expensive grade of stainless steel, can easily become bundled with the used drapes and gowns, and disposed inadvertently or otherwise.

In penal institutions such as jails and prisons, prisoners are encouraged to participate in various jobs and vocational training programs including welding, mechanics and machining. Some inmates, consequently, have access to machine tools and metal stock materials from which they might fashion weapons. Receptacles for trash and laundry, although necessary in the daily operations of such penal institutions, create the potential for the smuggling by inmates of weapons and potential weapon stock material from shop and training areas to other locations. Accordingly, the monitoring and search of such receptacles place a substantial burden on guards, and thus increases the operating costs of these institutions.

Metal detectors of various types are well known in the art. U.S. Pat. No. 3,065,412 discloses a metal detector useful in its detection of metallic impurities in powders, while U.S. Pat. No. 4,821,023 discloses a walk-through metal detector useful at airports. Thus, metal detection devices have been applied in a wide variety of uses in the past. U.S. Pat. Nos. 4,632,253 and 4,782,970 disclose devices that are specifically designed to detect the inadvertent disposal of cutlery into a trash container in restaurant environments. Both these patent references disclose devices which are design to cover trash containers, the first one of which utilizes an inductive probe to detect metal cutlery so as to close a flap to prevent its disposal into the trash container, while the latter reference discloses a magnetic arrangement which traps cutlery prior to being deposited into the receptacle.

U.S. Pat. No. 5,001,425 discloses a device designed to cover a receptacle for use in a hospital environment to detect the inadvertent disposal of metal articles in such a receptacle. As is pointed out therein, however, a significant problem in a hospital environment, and in particular surgical environments, is the presence of numerous metal objects surrounding the receptacle. Such metal objects proximate the detector can cause the inadvertent triggering of the detector alarm system without a metallic article having actually been placed therein due to false readings from metal articles immediately surrounding or near the top of such a receptacle. Thus, there remains a need for a metal detector that is designed to detect the inadvertent disposal of small metal objects into a receptacle in a hospital, prison or kitchen environment, which is reliable and designed to prevent false signals from being registered due to the presence of metal articles on or near the top or exterior of such a receptacle without having been placed therein.

SUMMARY OF THE INVENTION

Accordingly, it is one object of the present invention to provide a device to detect the inadvertent disposal of surgical instruments and other small metal articles into a receptacle to allow for their retrieval and reuse.

It is another object of the present invention to provide a device to assist in the monitoring of receptacles to prevent the unauthorized deposit of metal articles therein to prevent theft or the undetected transfer of metal articles using such receptacles.

It is yet another object of the present invention to provide a metal detector for receptacles useful in surgical operating rooms or kitchen environments for the detection of inadvertent disposal of metal articles therein while preventing false alarms or signals resulting from metal material or articles on or near such receptacles.

To achieve the foregoing and other objects and in accordance with the purpose of the present invention, as embodied and broadly described herein, a metal detection device is disclosed. The device includes a housing defining a central aperture. An induction member is mounted to the housing and surrounds the aperture for generating an output voltage in response to the presence of a metal object near the induction member. A mechanism is provided for calibrating the induction member by comparing its output voltage to a reference voltage to establish a threshold voltage which is unaffected by transient fluctuations in the output voltage. A device is disposed in the housing and spaced about the aperture for selectively sensing an object physically passing through the aperture. The sensing device generates a detection signal in response to passage of an object through the aperture only upon activation of the sensing device. A mechanism is provided for activating the sensing device upon generation of an inductive member output voltage above the threshold voltage. Finally, a mechanism is provided for triggering an alarm in response to the generation of the detection signal.

BRIEF DESCRIPTION OF THE DRAWINGS

The accompanying drawings which are incorporated in and form a part of the specification illustrate preferred embodiments of the present invention and, together with a description, serve to explain the principles of the invention. In the drawings.

DETAILED DESCRIPTION OF THE PREFERRED EMBODIMENT

Figure 1:
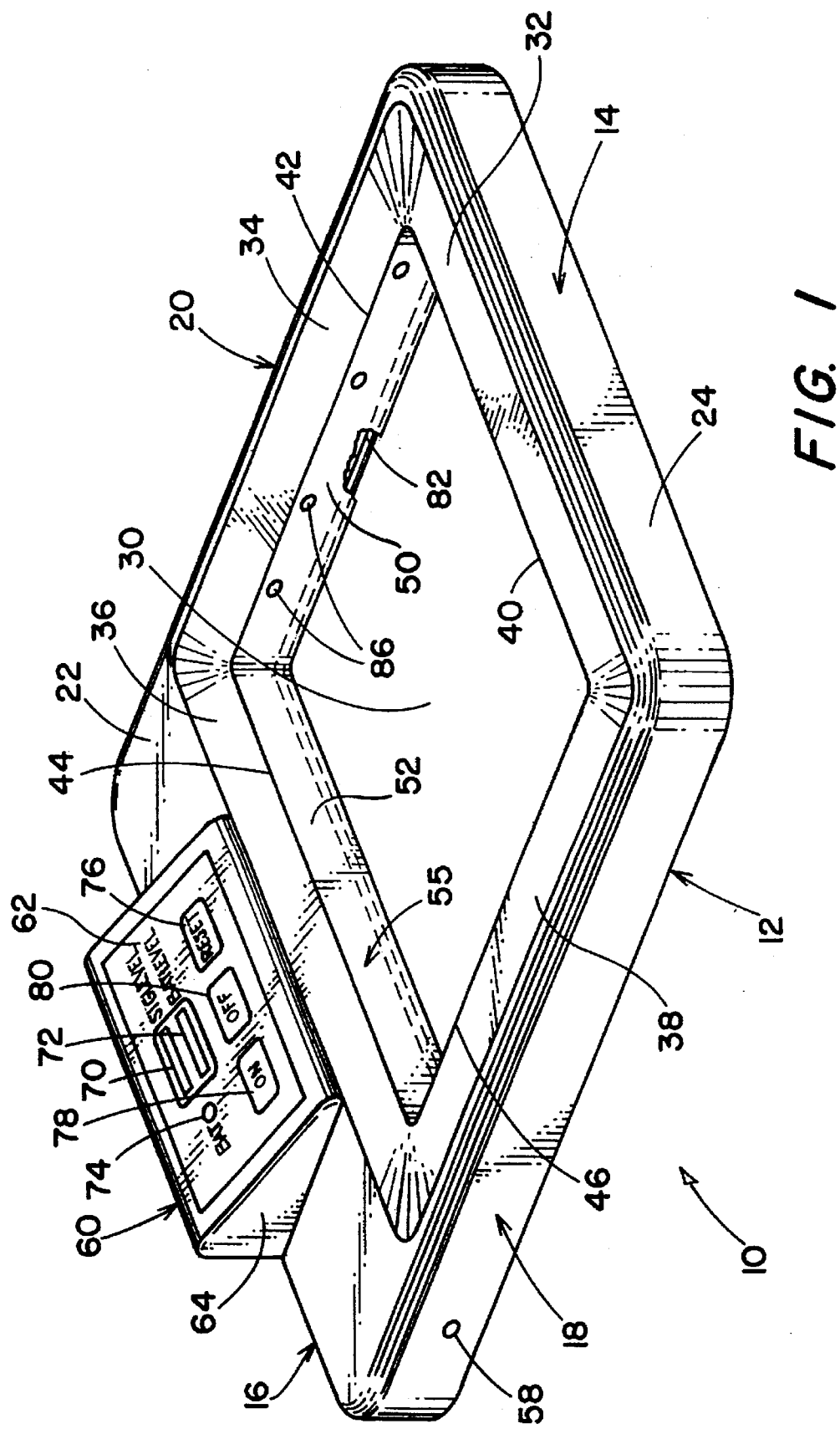
FIG. 1 is a front perspective view of the metal detector constructed in accordance with the present invention.
Figure 2:
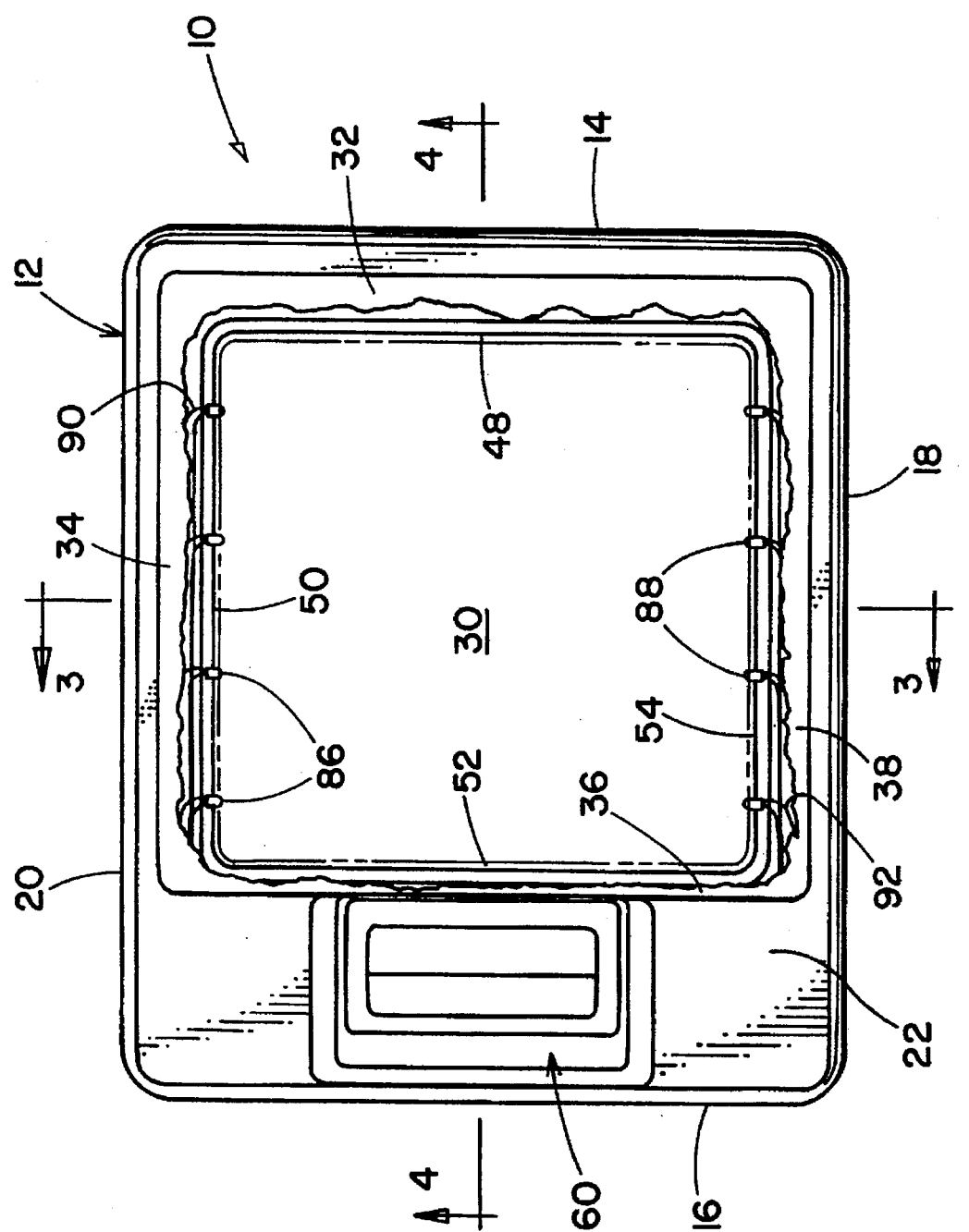
FIG. 2 is a top plan with some parts in section, of the detector device illustrated in FIG. 1.
Figure 3:
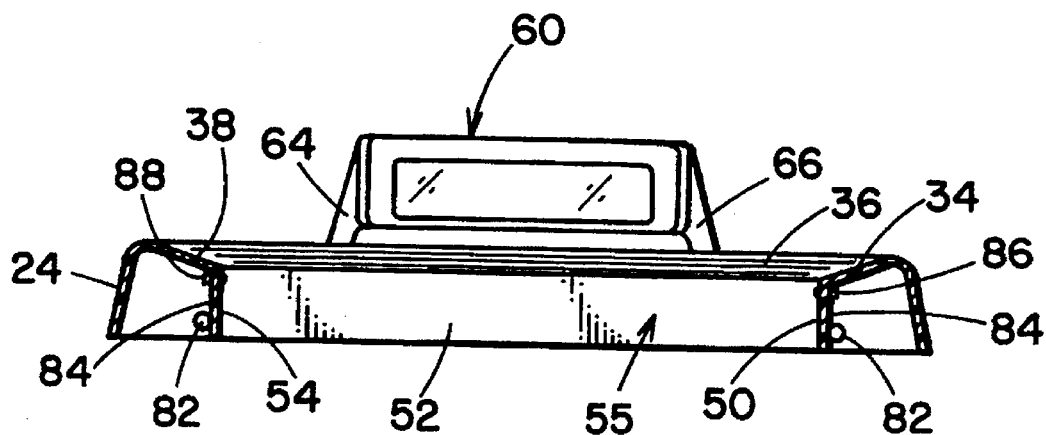
FIG. 3 is a cross-sectional view taken substantially along line 3—3 of FIG. 2.

Referring now to the drawings and in particular to FIGS. 1-5, a metal detector device 10 is disclosed and includes a housing 12 having a front portion 14, a rear portion 16 and two side portions 18 and 20, all of which are interconnected by a top surface 22. In preferred form, the housing 12 is substantially rectangular in shape and includes an exterior circumferential lip 24 that depends downwardly from the top surface 22 along the front and rear portions 14, 16 and the side portions 18, 20. The lip 24 provides a surface for mounting the housing 12 to a receptacle structure 26 which is designed to hold a waste disposal bag 28 as further described below.

The housing 12 is preferably constructed from any type of known non-metallic material and is most preferably constructed from molded plastic. In preferred form, the housing 12 is formed as an integral component in a rotational molding process wherein a powdered plastic resin material gradually melts within a heated, rotating mold. The liquefied resin then coats the interior surfaces of the mold to form the housing 12. After cooling, the housing 12 is then removed from the mold. In the instant case, the mold is preferably configured to produce two component parts simultaneously which are severed after removal from the mold. A preferred plastic resin material is polypropylene, although a wide variety of other plastics or non-ferrous materials may also be employed.

The housing 12 preferably includes a central aperture 30 which in preferred form is substantially square in shape. A plurality of inclined surfaces 32, 34, 36 and 38 depend angularly downwardly from the top surface 22 toward the aperture 30 and terminate at the respective edges 40, 42, 44 and 46. A plurality of flanges 48, 50, 52 and 54 each extend vertically downwardly from their respective side edges 40, 42, 44 and 46 to form a substantially square tube portion 55 defining the aperture 30. In use, the aperture 30 overlies and communicates with a top opening of a waste disposal bag 28. Accordingly, the inclined surfaces 32-38, the tube 55 and the aperture 30 facilitate the deposit of articles and material into the disposal bag 28 carried by the receptacle 26.

A pair of pivot arms 56 are preferably secured to the side edges 18, 20 of the housing 12 by a pair of mounting pins 58 in order to secure the housing 12 to the receptacle 26 in a hinged manner as described in greater detail below. In this manner, the housing 12 may be pivoted away from the disposal bag 28 in order to remove the disposal bag 28 from the receptacle 26 when it is full.

A control console 60 extends upwardly from a rear portion of the top 22 of housing 12 and preferably includes a downwardly and forwardly inclined control panel 62 surrounded by side members 64, 66. As particularly illustrated in FIG. 4, a hollow interior control box 68 is disposed within the interior of the console 60 and forms a housing for the electronic components of the metal detector 10 as described in greater detail below.

The control panel 62 preferably includes a peak-hold type LCD bar graph 70 for displaying voltage levels induced in the detection circuitry by the deposit of metal articles through the aperture 30 of the housing 12 in order to allow an operator to estimate the size of the metal article disposed. Thus, an insignificant metal object such as a surgical staple or the like would provide a low signal level and would not set off the alarm as described in greater detail below, while a large and expensive surgical instrument would provide a high signal level and set off the alarm. The peak-hold feature causes the graph 70 to maintain the display for a time sufficient to enable operator inspection. In addition, a similar LCD bar graph 72 provides an indication of battery voltage to allow an operator to estimate the remaining battery life for the unit 10. Finally, an LED low battery indicator 74 provides a positive indication of the need to recharge the batteries for the detector 10.

The metal detector 10 is designed for ease of operation with minimal training. Toward this end, user friendly controls preferably comprise three buttons including a reset button 76, an "on" button 78 and an "off" button 80. The reset button 76 is designed to silence an audible alarm after detection of a metal article and to reset the metal detector for continued use. The "on" button 78 activates the power to the device 10 while the "off" button 80 deactivates the power source. The control panel 62 is preferably of a flexible membrane type commonly employed in microwave ovens in which the control buttons 76, 78 and 80 comprise zones designated by indicia which do not protrude above the panel 62. The LCD bar graph displays 70 and 72 and the LED light 74 underlie the panel 62 and are displayed through transparent windows. Panels of this type are custom fabricated pursuant to customer specification by any number of vendors, and are well known to the art.

In preferred form, an induction member in the form of a detection coil 82 surrounds the aperture 30 and is designed to detect the presence of metal proximate thereto particularly as it passes through the aperture 30. The detection coil 82 is preferably mounted to the outside surfaces 84 of the tube portion 55 which defines the aperture 30. In preferred form, the detection coil 82 is mounted proximate to the lowermost edges of the flanges 48-54 and is secured in any manner thereto. In one form, a notch (not illustrated) may be formed in the surfaces 84 in which a coil member 82 may be wound. While any type of induction member suitable for use in the present invention may be utilized as the detection coil 82, it is preferred that the detection coil 82 includes a primary coil which is 26 gauge copper wire wound sixteen turns about the aperture 30 and a secondary coil which is also 26 gauge copper wire wound six rams about the aperture 30. In this manner, when a metal object moves physically near the detection coil 82, it causes a change in the electromagnetic field surrounding the coil 82, and this causes a change in the current described below. This is true, however, whether the metal article is proximate the coil 82 by being placed through the aperture 30 or proximate the coil 82 by being placed against, on top or even nearby the housing 12.

In order to insure that the detector 10 only detects metal articles passing through the aperture 30 and avoids any false readings from metal articles passing near the detection coil 82 outside the exterior housing 12, a mechanism for sensing an object, metallic or otherwise, physically passing through the aperture 30 is disposed about the aperture 30. In preferred form, this mechanism includes a plurality of pulse emitting members 86 which preferably are in the form of light emitting diodes (LED's), and a plurality of pulse detecting members 88 preferably in the form of infrared phototransistors. While the preferred form of the members 86, 88 include infrared LED's and infrared phototransistors, ultrasound emitters and detectors may also be utilized. Preferably, there are sufficient numbers of pulse emitting members 86 disposed along one flange 50 and sufficient numbers of pulse detection members 88 disposed along the opposite flange 54 in order to span the entire cross-sectional area of the aperture 30. The pulse emitting members 86 are preferably positioned proximate the edge 42 away from the coil 82 to minimize electrical interferences and are interconnected to the electronic components of the console 60 by wiring 90. Likewise the pulse detecting members 88 are positioned proximate the edge 46 away from the coil 82 and are connected to the console 60 by wiring 92. In preferred form, there are equal numbers of pulse emitting members 86 and pulse detecting members 88 aligned opposite each other so that as an object passes through the aperture 30, it physically interferes with the detection by at least one member 88 of a pulse being emitted from the members 86, and this interference is monitored by the members 88 and signaled to the control panel 60 in a manner described below.

In preferred form, a rechargeable nickel-cadmium or nickel metal hydride battery 94 provides all operating power for the detection circuitry of the device 10. A jack 96 extends through the rear portion 16 and allows connection of the battery 94 to a conventional recharging device in a conventional manner.

In general, the device 10 of the present invention operates by powering the detection coil 82 so as to create a magnetic field surrounding it. If a metal member passes proximate to the detection coil 82, a change is detected in the electromagnetic field therein. A mechanism, described in greater detail below, calibrates the detection coil 82 by comparing the output voltage thereof caused by a change in the electromagnetic field thereabout to a reference voltage to establish a threshold voltage which is unaffected by transient fluctuations in the coil output voltage as described below. When the threshold voltage of the detection coil 82 is exceeded, an electric signal is generated to simultaneously activate the pulse emitting members 86. If all the pulse emitting members 86 are detected by the pulse detection members 88, nothing happens since it is clear that an object has not passed through the aperture 30, and that the threshold voltage activated by the detection coil 82 was the result of a metal member passing near but outside the housing 12. However, should the threshold voltage of coil 82 be exceeded so as to activate the pulse emitting members 86, and one or more of the pulse detection members 88 is not activated, an alarm is triggered in response to the lack of activation by one or more of the pulse detection members. The only manner in which a pulse detection member 88 would not be activated is due to the physical blockage of the pulse emitted from a member 86 to prevent its paired member 88 from receiving and detecting the pulse. In addition, since the pulse emitting members 86 are only activated or turned on when the threshold voltage of the coil 82 is surpassed, non-metallic objects can consistently pass through the aperture 30 without generating an alarm signal since the pulse emitting members 86 are in a nonactive state. Consequently, the combination of the detection coil 82, the pulse emitting members 86 and the pulse detection members 88 and the circuitry interconnecting the same prevents false signals caused by metallic objects exterior to but proximate the detector 10 from being generated.

Figure 4:
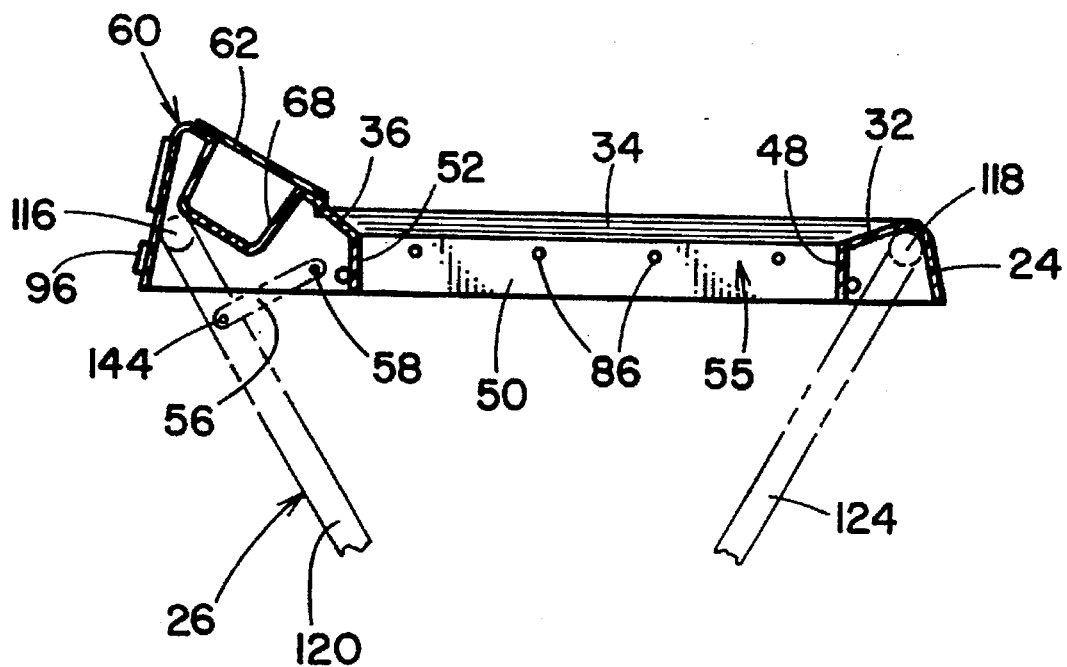
FIG. 4 is cross-sectional view taken substantially along line 4—4 of FIG. 2 and illustrating placement of the device onto a receptacle support member.
Figure 5:
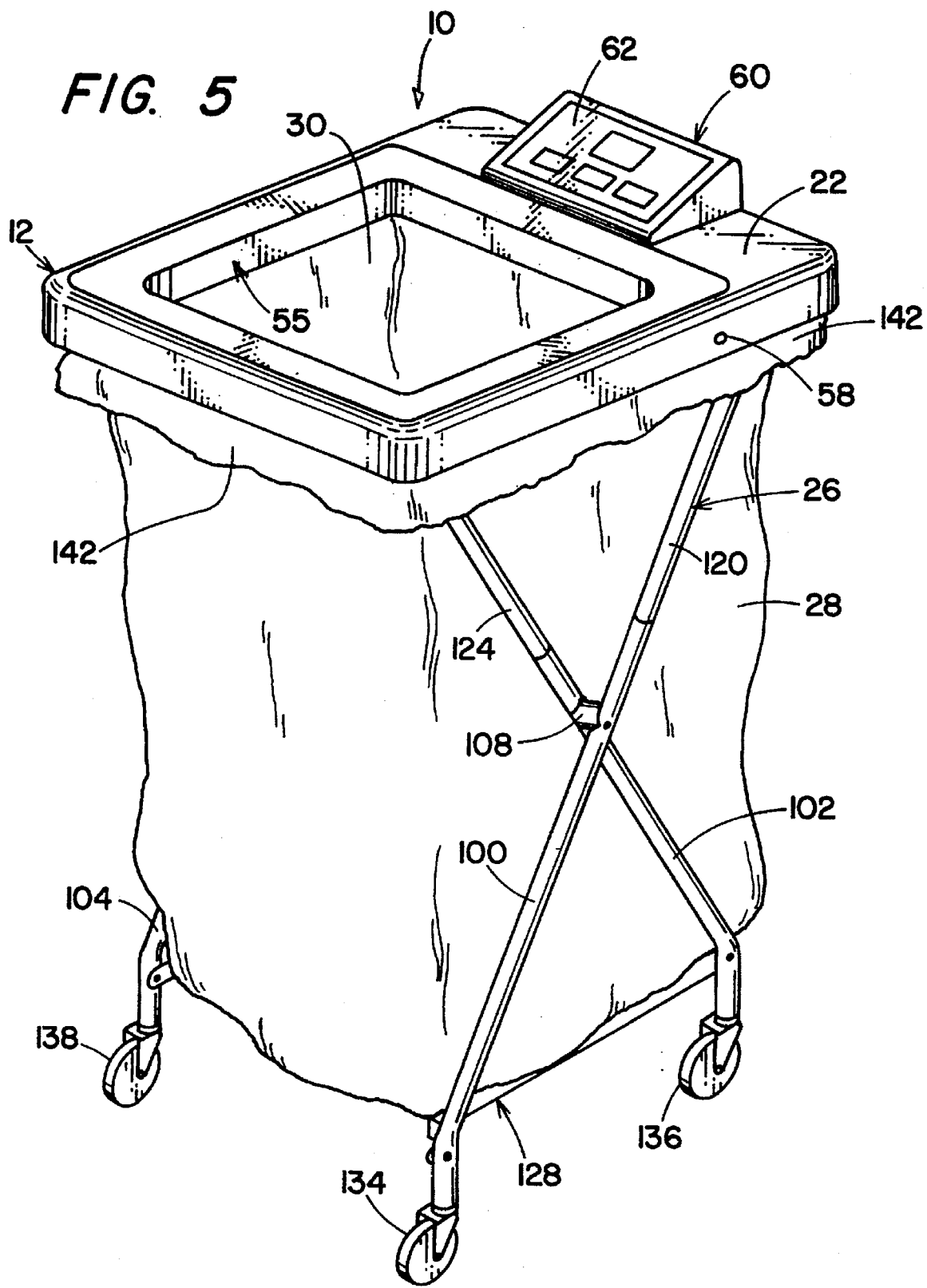
FIG. 5 is a side perspective view of the detector device constructed in accordance with present invention mounted onto a portable receptacle member.
Figure 6:
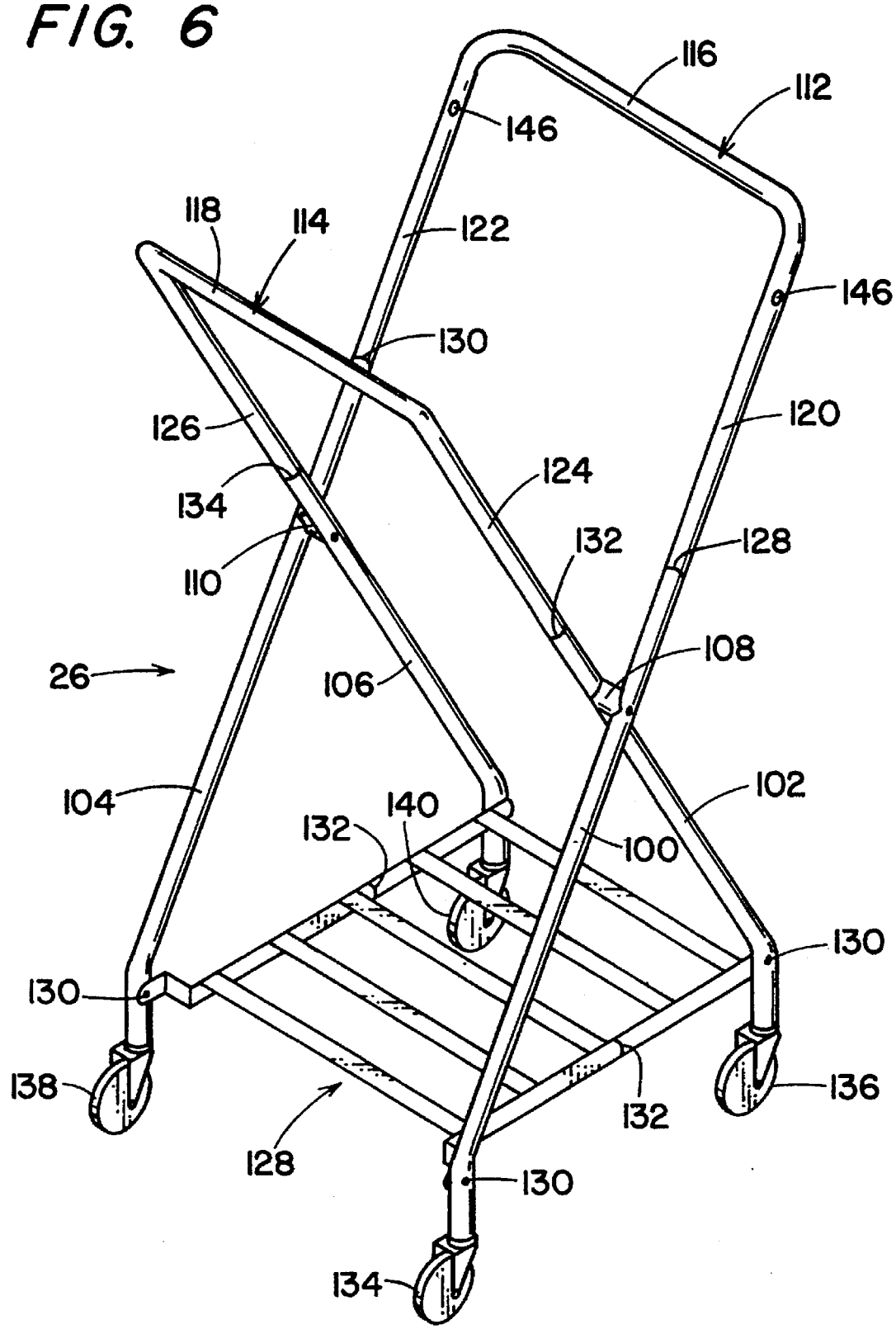
FIG. 6 is a side perspective view of the receptacle member illustrated in FIG. 5 without the receptacle bag and the detector device mounted thereon.
Figure 7:
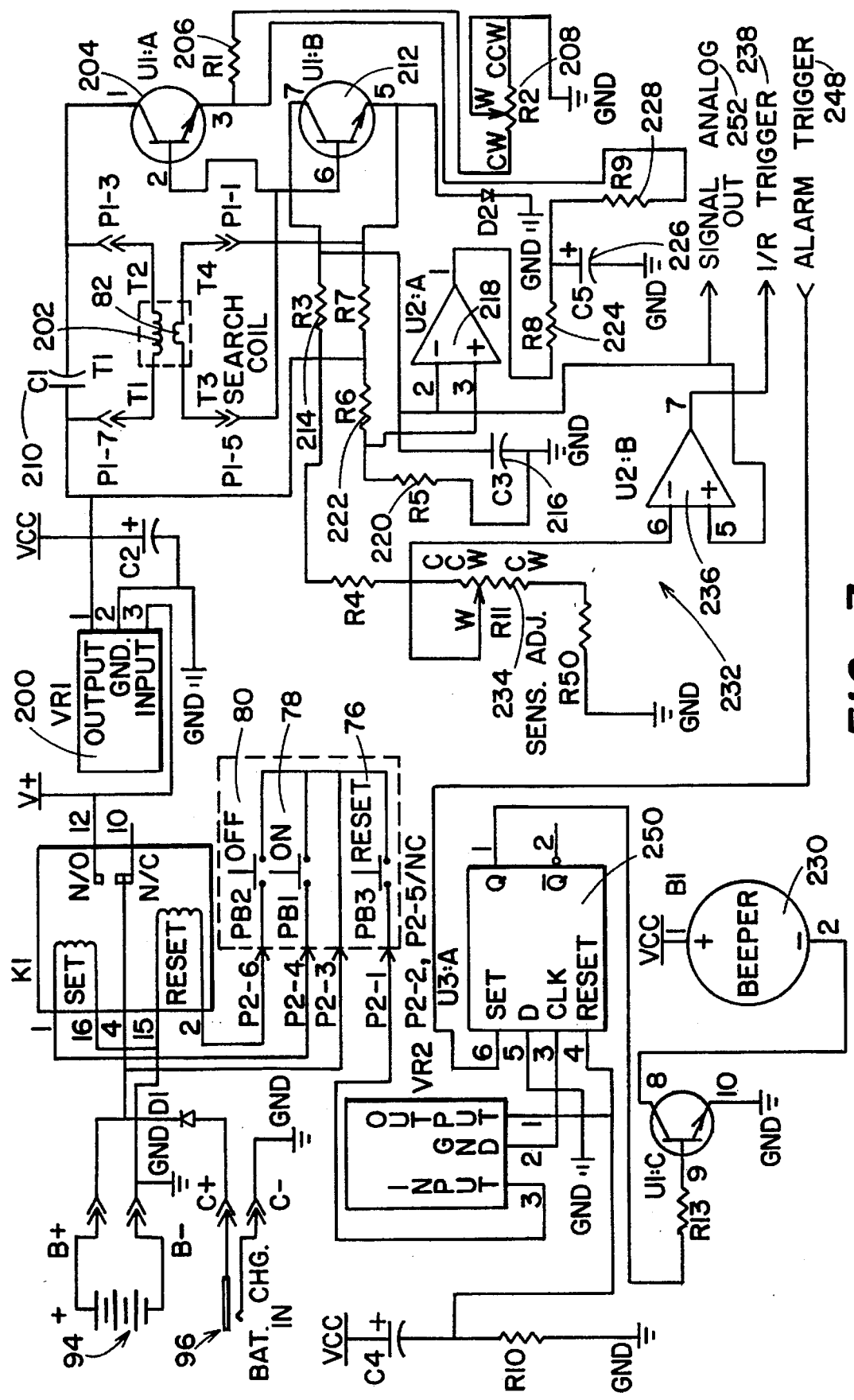
FIG. 7 is schematic diagram illustrating the circuitry of the metal detector of the present invention.
Figure 8:
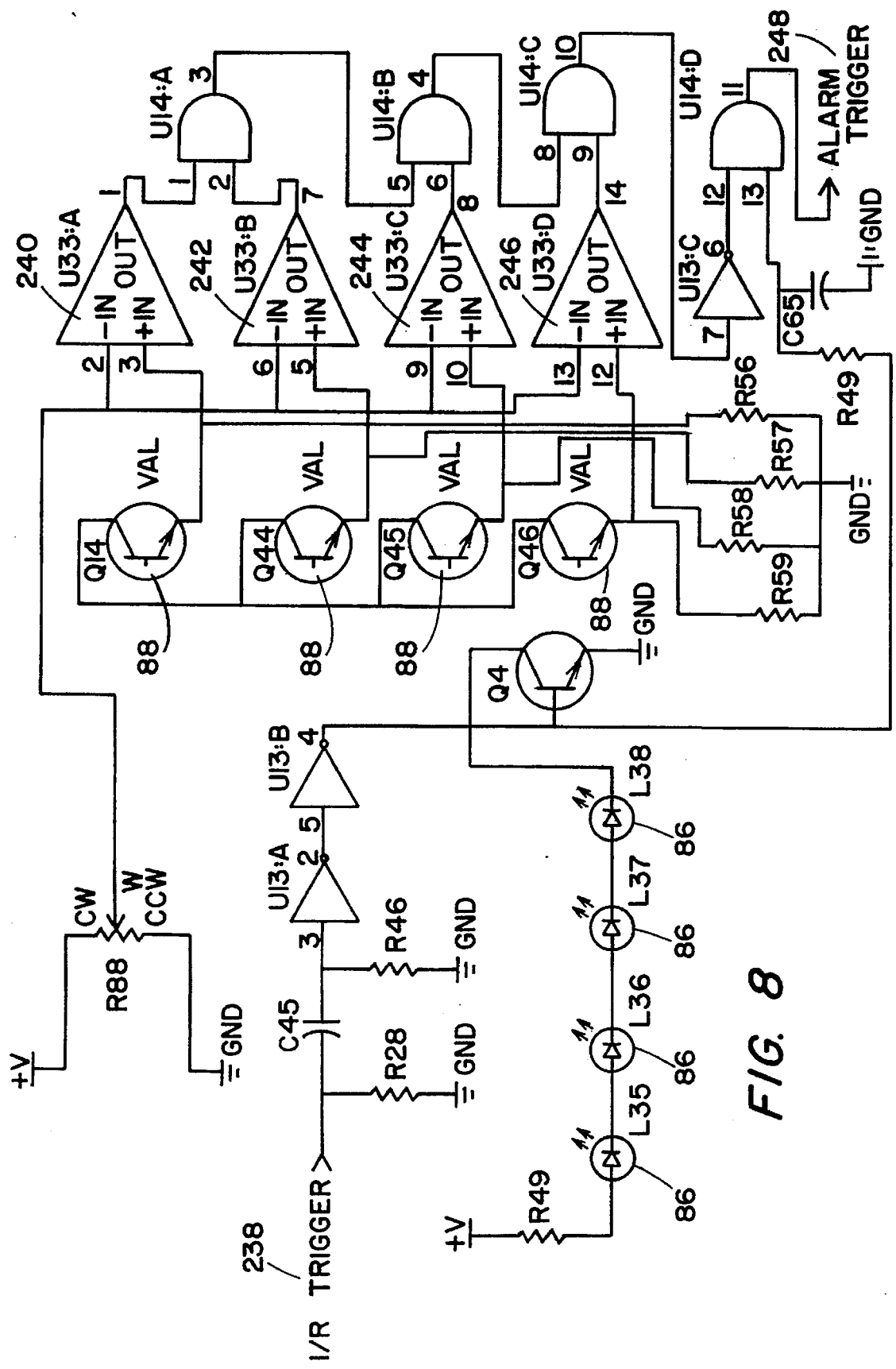
FIG. 8 is schematic diagram illustrating the circuitry of the LED emission and reception portion of the metal detector the present invention.
Figure 9:
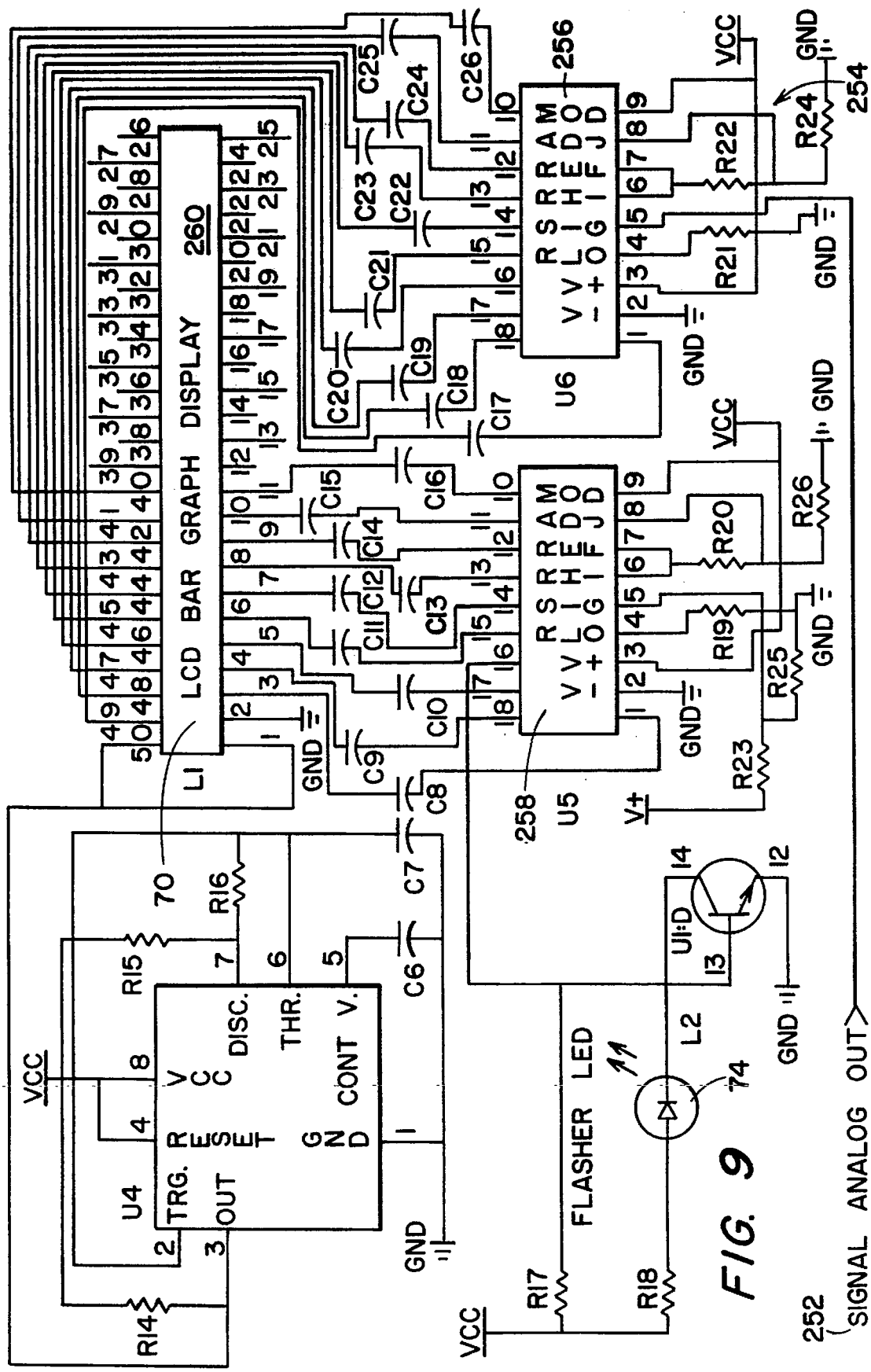
FIG. 9 is a schematic diagram illustrating a bar graph display and associated driver circuitry for displaying detector signal strength and battery voltage of the metal detector of the present invention.

With particular reference to FIGS. 4–6, a typical cart or receptacle structure 26 is illustrated for holding a waste disposal bag 28 for use in conjunction with the metal detector 10. It should be understood, however, that the metal detector 10 of the present invention may be utilized with any type of receptacle and may be modified to fit the desired end use whether it be in a hospital environment, a penal institution, a kitchen environment or the like. The receptacle 26 typically includes four tubular lower leg members 100, 102, 104 and 106 that are pivotally connected together in pairs by pivotal connection members 108 and 110. The pivotal connection members 108, 110 may include rivets, pins, bolts, screws or any other appropriate member pivotally interconnecting legs 100 to 102 and 104 to 106.

The upper portions of the receptacle 26 include a pair of substantially U-shaped members 112, 114 secured to the upper portion of legs 100, 104 and 102, 106, respectively. Preferably, each U-shaped portion 112, 114 includes, respectively, a substantially transverse crossbar member 116, 118 extending between respective side frame bars 120, 122 and 124, 126. Interengaging telescoping connections 128, 130, 132 and 134 removably connect the side frame bars 120, 122, 124 and 126 to their respective lower leg members 100, 104, 102 and 106, respectively. This detachable construction, in conjunction with pivotal connections 108, 110, allows the receptacle 26 to be collapsed for shipping and storage, yet readily assembled without the use of tools. Preferably, the upper U-shaped portions 112, 114 are formed from a non-metallic material such as PVC plastic tubing in order to minimize interference with the metal detector's circuitry. The lower components of the receptacle 26 may be formed from a lightweight tubular metal material such as aluminum tubing. A bag support rack 128 includes four corner portions pivotally connected at 130 to lower end portions of the leg members 100, 102, 104 and 106. In addition, the rack 128 has a two-piece construction, with side rail members bifurcated at abutting joints 132. Accordingly, the two rack halves may be folded upwardly for storage and transportation of the receptacle 26. The leg members 100, 102, 104 and 106 terminate in respective casters 134, 136, 138 and 140 which allow the receptacle 26 to be easily rolled to a desired location for use. In use, a medical waste disposal bag 28 is placed on the rack 128 with the upper side portions 142 of the bag 28 folded outwardly over the crossbars 116, 118 to maintain the mouth of the bag 28 in an open condition for access by the aperture 30 of the device 10.

With reference to the FIGS. 4–6, the housing 12 is pivotally connected to the receptacle 26. A hinge member 56 in the form of an aluminum strut has a first end pivotally secured by a fastener 58 to the side portion 18 of the housing 12. A second fastener 144 secures an opposite end of the pivot strut 56 to the aperture 146 in the upper portions of the side frame members 120. Fasteners 58 and 144 may take the form of bolts, screws, rivets or pins. It should be understood that identical pivotal struts and fastener assemblies 56 are secured on both sides of the housing 12 and attach both side portions 18, 20 of the housing 12 to the tubes 120, 122 of the receptacle 26. By virtue of this compound physical linkage, the entire housing 12 may thus be pivoted along an arc between a closed position as illustrated in FIG. 5 wherein the housing 12 is securely fixed about the transverse crossbars 116 and 118 of the receptacle 26 and the aperture 30 opens directly to the open end of the bag 28, and an open position. The open position is illustrated in the cross-referenced parent patent application and is designed to rotate the front end member 14 away from engagement with the transverse crossbar 118 and rotate the housing 12 greater than 90° so as to gain full access to the open end of the bag 28 without passing through the aperture 30 or in any manner being hindered by the device 10. Thus, it should be noted that the housing 12 and the receptacle 26 are preferably complementary dimensions such that the crossbars 116, 118 of the receptacle 26 nest within the housing 12 at the rear 16 and front-end portions 14, respectively.

Referring now in particular to FIGS. 1 and 7–9, the electronic components of the metal detector 10 will now be described. As previously described, a jack 96 allows connection of the battery 94 to a conventional recharging device in a conventional manner. A latching relay K1 controlled by the "on" push button 78 and the "off" push button 80 provides for connection and disconnection of the battery 94 to the electronic detection circuitry. In the "on" position, the voltage regulator 200 reduces the battery voltage V+ to a reduced regulated voltage VCC.

The detection circuitry includes a primary coil 202 through which the current initially flows. The conduction of the transistor 204, resistor 206 and variable resistor 208 control the current through the primary coil 202. The momentary current through the primary coil 202 induces a voltage in the secondary coil of the detector coil 82 which controls the conduction of the transistor 204 which in turn again pulses current through the primary coil 202. The frequency of the oscillations is determined by the parallel resonant frequency of the primary coil 202 and the capacitor 210. The voltage of the detector coil 82 also controls the conduction of a transistor 212 which generates a DC voltage through resistor 214 and capacitor 216 which is directly proportional to the induced voltage in the detector cot 82. When a metal object enters the magnetic field of the primary coil 202 and the detector coil 82, eddy currents are produced in that object which in turn affect the magnetic field and the induced voltage in the detector coil 82. This change is detected in the DC voltage.

The detector circuitry further includes an auto calibration feature which prevents drift and maintains the accuracy of the detector over time while preventing environmental fluctuations therein from impairing detector performance. An amplifier 218 compares the DC voltage from the transistor 212 (pin 7) with a reference voltage set up by resisters 220 and 222. The amplifier output swings high or low and is integrated through resistor 224 and capacitor 226. The output then conducts through the resistor 228 back to the transistor 204, which influences the amount of current pulsed through the primary coil 202. The action of this network maintains the DC voltage at transistor 212 to match the reference voltage at the amplifier 218. Since fluctuations are integrated over time, the network does not react to environmental changes but only to long term changes, and thus serves to stabilize the sensitivity of the metal detector 10.

The metal detector 10 includes an audio alarm 230 as well as the LCD bar graph visual display 260 to alert an operator of the passage of a significant metal object through the aperture 30 by the detector coil 82. A threshold detector 232 includes a variable resistor 234 and amplifier 236 and compares the voltage induced in the detector coil 82 with a threshold reference voltage established by the resistor 234. If the detector coil voltage exceeds the threshold reference voltage, the amplifier 236 generates a trigger signal 238. The variable resistor 234 may be set to vary the threshold voltage to permit the passage of small metal objects, such as staples or foil, through the aperture 30 without generating trigger signal 238. The preferred pulse generation members are in the form of four infrared LED's 86 which are connected in series and are pulsed simultaneously by the trigger signal 238. The pulse receiving members 88 are preferably in the form of infrared phototransistors. Amplifiers 240, 242, 244 and 246 read the voltage outputs of the four phototransistors 88. So long as all four phototransistors 88 are activated by the reception of light emitted by the four LED's 86, nothing happens. However, if one of the amplifiers 240–246 does not register a voltage output by its corresponding phototransistor 88 while the remaining amplifiers do so register output by the remaining phototransistors 88, then an alarm signal 248 is generated since the light from one of the LED's 86 has been blocked from reception by a phototransistor 88 due to the physical presence of an object in the aperture 30.

If an alarm signal 248 is generated, a latch 250 is set and activates the audio alarm 230. The external reset button 76 for the latch 250 shuts off the alarm. When the trigger signal 238 is activated, an additional signal 252 is generated and is directed to a real time voltage circuit 254 which processes the voltage induced in the detector coil 82 and outputs the voltage to the analog input of a bar graph driver 256. The bar graph driver 256 displays the real time voltage on one portion 70 of a dual bar graph LCD display 260. A second bar graph driver 258 displays the battery voltage V+ on the other portion 72 of the LCD display 260 and also pulses the low battery LED 74 if the battery voltage V+ falls below a predetermined limit.

As can be seen from the above, the present invention provides for a portable metal detector unit that is useful in a wide variety of environments including hospital surgery rooms, prisons, kitchens or high security areas to prevent the inadvertent disposal or the intentional hiding of metal objects in receptacles. The device of the present invention is removably attachable to a wide variety of types of receptacles and can be moved out of the way in order to easily replace receptacle bags. Moreover, since the present invention is portable and may therefore come into the physical presence of large metal objects exterior to the device, the present invention is designed to prevent inadvertent triggering of the alarm system by the presence of such metal objects outside of the aperture of the device. Thus, only a metal object moving through the aperture of the device can set off the alarm of the present invention thereby signaling the inadvertent or improper placement of a metal object within the receptacle bag. The present invention prevents the inadvertent loss of expensive surgical instruments or kitchen utensils thus providing substantial savings to hospitals, restaurants and the like. Moreover, the present invention prevents the smuggling of metal objects from one room to another by their placement in a receptacle. Nonetheless, people utilizing the device of the invention are not hampered by improper signals due to the passage of very small metal objects through the aperture or the presence of metal objects immediately outside the device due to its built in safeguard system.

The foregoing description and the illustrative embodiments of the present invention have been described in detail in varying modifications and alternate embodiments. It should be understood, however, that the foregoing description of the present invention is exemplary only, and that the scope of the present invention is to be limited to the claims as interpreted in view of the prior art. Moreover, the invention illustratively disclosed herein suitably may be practiced in the absence of any element which is not specifically disclosed herein.

I claim:

1. A metal detection device comprising:
   a housing defining a central aperture;
   an induction member mounted to said housing and surrounding said aperture for generating an output voltage in response to the presence of a metal object near said induction member;
   means for calibrating said induction member by comparing said output voltage to a reference voltage to establish a threshold voltage which is unaffected by transient environmental fluctuations in said output voltage;
   means disposed in said housing and spaced about said aperture for selectively sensing an object passing through said aperture, said sensing means generating a detection signal in response to passage of an object through said aperture only upon activation of said sensing means;
   means for activating said sensing means upon generation of an inductive member output voltage above said threshold voltage; and
   means for triggering an alarm in response to the generation of said detection signal.

2. The device as claimed in claim 1, wherein said induction member comprises an electromagnetic detection coil.

3. The device as claimed in claim 1, wherein said object sensing means comprises pulse emission means positioned on one side of said aperture and pulse reception means positioned on an opposite side of said aperture for generating said detection signal.

4. The device as claimed in claim 3, wherein said pulse emission means comprises a plurality of infrared light emitting diodes, and said pulse reception means comprises a plurality of infrared phototransistors.

5. The device as claimed in claim 4, wherein said light emitting diodes and said phototransistors are spaced opposite each other in paired relationship to span the entire opening of said aperture.

6. The device as claimed in claim 3, wherein said pulse reception means generates said detection signal only upon failure of one or more of said pulse reception means to register emissions from a paired, activated pulse emission means, thereby indicating blockage of said pulse emission means by an object passing through said aperture.

7. The device as claimed in claim 1, wherein said means for activating said sensing moans comprises an electrical circuit for generating an electric pulse to said sensing means upon generation of an induction member output voltage in excess of said threshold voltage.

8. The device as claimed in claim 7, wherein said sensing means is activated less than 10 microseconds after generation of said threshold output voltage.

9. The device as claimed in claim 8, wherein said sensing means is activated for approximately 20 microseconds.

10. The device as claimed in claim 1, wherein said alarm comprises visual and audio alarms.

11. The device as claimed in claim 1, wherein said housing is sized and shaped to removably cover an open-ended receptacle wherein said aperture is aligned with the open end of said receptacle to detect the passing of metal objects into said receptacle through said aperture.

12. A metal detection device comprising:
    a housing defining a central aperture;
    a detection coil mounted to said housing and surrounding said aperture for generating an output voltage when a metal object is passed near said coil;
    means for automatically calibrating said detection coil by comparing said output voltage to a reference voltage to establish a threshold voltage output which ignores transient environmental fluctuations in said coil output voltage;
    a plurality of pulse emitting members spaced along a first side portion of said housing aperture;
    a plurality of pulse reception members spaced along a second side portion of said housing aperture opposite said first side portion to receive and sense the output of said pulse emitting members upon activation thereof;
    means for simultaneously activating said pulse emitting members upon generation of a coil output voltage above said threshold voltage; and
    means for triggering a detection signal when at least one of said pulse reception members fails to register the output of one or more pulse emitting members upon simultaneous activation of said pulse emitting members.

13. The device as claimed in claim 12, wherein the output of said pulse emitting members comprises light or ultrasonic waves, with said pulse reception members receiving and registering the same.

14. The device as claimed in claim 13, wherein said pulse emitting members comprise infrared light emitting diodes, and said pulse reception members comprise infrared phototransistors.

15. The device as claimed in claim 13, wherein said pulse emitting members and pulse reception members are present in sufficient numbers to span the entire width of said aperture to detect any object passing through any portion of said aperture.

16. The device as claimed in claim 15, wherein said pulse emitting members and pulse reception members are aligned in pairs.

17. The device as claimed in claim 12, wherein said pulse emitting members are simultaneously activated within about 10 microseconds following the generation of said coil output voltage in excess of said threshold voltage output level.

18. The device as claimed in claim 17, wherein said pulse emitting members are activated for approximately 20 microseconds, the nonregistration of the output of at least one pulse emitting member at one said pulse reception member indicating the physical presence of a metal object passing through said aperture.

19. The device as claimed in claim 12, wherein said housing is sized and shaped to removably cover an open-ended receptacle wherein said aperture is aligned with the open end of said receptacle to detect the passing of metal objects into said receptacle through said aperture.

20. A device for detecting metal objects as they are inserted into a receptacle having an open upper end, said device comprising:

a housing sized and shaped to cover said receptacle open upper end, said housing defining a central aperture for access to said open upper end;

inductive means disposed within said housing surrounding said aperture for generating an output voltage when a metal object passes proximate thereto;

means for automatically calibrating said induction means by comparing said output voltage to a reference voltage to provide a threshold voltage which is unaffected by transient environmentally induced fluctuations in said output voltage;

means disposed in said housing and spaced about said aperture for selectively sensing the presence of an object passing through said aperture, said sensing means generating an electric signal in response thereto upon activation of said sensing means;

means for activating said sensing means upon generation of an inductive means output voltage above said threshold voltage; and means for triggering an alarm detection signal in response to generation of said sensing means electric signal.

21. The device as claimed in claim 20, wherein said housing includes means for mounting said housing to said receptacle between an open position allowing access to said receptacle and a closed position for substantially covering said receptacle open upper end except through said aperture.

22. The device as claimed in claim 20, wherein said inductive moans comprises an electromagnetic detection coil.

23. The device as claimed in claim 22, wherein said sensing means comprises a plurality of pulse emission members positioned along one side portion of said aperture and a plurality of pulse reception members positioned on the opposite side portion of said aperture to scan the entire width of said aperture.

24. The device as claimed in claim 23, wherein said pulse emission members comprise infrared light emitting diodes and said pulse reception members comprise infrared phototransistors.

25. The device as claimed in claim 22, wherein said signal triggering means is adapted to activate upon failure of at least one said pulse reception member to detect emissions from at least one said pulse emission member upon activation thereof thereby indicating the physical presence of an object in said aperture blocking the pulse emissions.

* * * * *